(12) United States Patent
Beer

(10) Patent No.: US 8,241,488 B2
(45) Date of Patent: Aug. 14, 2012

(54) AUTO-CALIBRATING TEST SENSORS

(75) Inventor: Greg P. Beer, Cassopolis, MI (US)

(73) Assignee: Bayer HealthCare LLC, Tarrytown, NY (US)

( * ) Notice: Subject to any disclaimer, the term of this patent is extended or adjusted under 35 U.S.C. 154(b) by 281 days.

(21) Appl. No.: 12/249,283

(22) Filed: Oct. 10, 2008

(65) Prior Publication Data

US 2009/0113981 A1    May 7, 2009

Related U.S. Application Data

(60) Provisional application No. 61/002,052, filed on Nov. 6, 2007.

(51) Int. Cl.
*G01N 27/327* (2006.01)
(52) U.S. Cl. .......... 205/792; 204/403.02; 156/269
(58) Field of Classification Search ........... 204/403.01, 204/403.02; 205/792, 777.5; 156/238, 269
See application file for complete search history.

(56) References Cited

U.S. PATENT DOCUMENTS

| | | | |
|---|---|---|---|
| 4,510,383 A | 4/1985 | Ruppender | |
| 4,714,874 A | 12/1987 | Morris et al. | |
| 4,929,426 A | 5/1990 | Bodai et al. | |
| 4,940,945 A | 7/1990 | Littlejohn et al. | |
| 5,194,393 A | 3/1993 | Hugl et al. | |
| 5,281,395 A | 1/1994 | Markart et al. | |
| 5,379,214 A | 1/1995 | Arbuckle et al. | |
| 5,443,080 A | 8/1995 | D'Angelo et al. | |
| 5,445,967 A | 8/1995 | Deuter | |
| 5,462,064 A | 10/1995 | D'Angelo et al. | |
| 5,489,414 A | 2/1996 | Schreiber et al. | |
| 5,510,266 A | 4/1996 | Bonner et al. | |
| 5,518,689 A | 5/1996 | Dosmann et al. | |
| 5,575,403 A | 11/1996 | Charlton et al. | |
| 5,580,794 A | 12/1996 | Allen | |
| 5,597,532 A | 1/1997 | Connolly | |
| 5,611,999 A | 3/1997 | Dosmann et al. | |
| 5,780,304 A | 7/1998 | Matzinger et al. | |

(Continued)

FOREIGN PATENT DOCUMENTS

EP    0840122    5/1998

(Continued)

OTHER PUBLICATIONS

Machine translation of JP 2001-281197, Oct. 2001.*

(Continued)

*Primary Examiner* — Kaj K Olsen
(74) *Attorney, Agent, or Firm* — Nixon Peabody LLP

(57) ABSTRACT

An electrochemical test sensor configured to determine an analyte concentration of a fluid sample comprises a base including a first end, a second opposing end, a first side and a second side bridging the first and second opposing ends. The test sensor further comprises a plurality of electrodes formed on the base at or near the first end. The plurality of electrodes includes a working electrode and a counter electrode. The sensor further comprises a first test-sensor contact formed on the base at or near the second opposing end and coupled to the working electrode by a first conductive lead. The sensor further comprises a second test-sensor contact formed on the base at or near the second opposing end and coupled to the counter electrode by a second conductive lead. The positions of the first and second test-sensor contacts correspond with calibration information assigned to the test sensor.

14 Claims, 4 Drawing Sheets

U.S. PATENT DOCUMENTS

| | | | |
|---|---|---|---|
| 5,795,543 A | 8/1998 | Poto et al. | |
| 5,830,133 A | 11/1998 | Osten et al. | |
| 5,837,546 A | 11/1998 | Allen et al. | |
| 5,856,195 A | 1/1999 | Charlton et al. | |
| 5,863,800 A | 1/1999 | Eikmeier et al. | |
| 5,866,349 A | 2/1999 | Lilja et al. | |
| 5,945,341 A | 8/1999 | Howard, III | |
| 5,962,215 A | 10/1999 | Douglas et al. | |
| 6,103,033 A * | 8/2000 | Say et al. | 156/73.1 |
| 6,168,957 B1 | 1/2001 | Matzinger et al. | |
| 6,270,637 B1 * | 8/2001 | Crismore et al. | 204/403.04 |
| 6,335,203 B1 | 1/2002 | Patel et al. | |
| 6,377,894 B1 | 4/2002 | Deweese et al. | |
| 6,441,898 B1 | 8/2002 | Markart | |
| 6,485,437 B1 | 11/2002 | Tapper | |
| 6,558,528 B1 * | 5/2003 | Matzinger | 205/777.5 |
| 6,599,406 B1 | 7/2003 | Kawanaka et al. | |
| 6,645,359 B1 | 11/2003 | Bhullar et al. | |
| 6,662,439 B1 | 12/2003 | Bhullar | |
| 6,767,440 B1 | 7/2004 | Bhullar et al. | |
| 6,770,487 B2 | 8/2004 | Crosby | |
| 6,773,671 B1 | 8/2004 | Lewis et al. | |
| 6,814,844 B2 | 11/2004 | Bhullar et al. | |
| 6,827,829 B2 | 12/2004 | Kawanaka et al. | |
| 6,866,758 B2 * | 3/2005 | Bhullar et al. | 204/403.02 |
| 6,875,327 B1 | 4/2005 | Miyazaki et al. | |
| 2001/0023324 A1 | 9/2001 | Pronovost et al. | |
| 2001/0039057 A1 | 11/2001 | Douglas et al. | |
| 2001/0045355 A1 | 11/2001 | Gephart et al. | |
| 2002/0059030 A1 | 5/2002 | Otworth et al. | |
| 2002/0082797 A1 | 6/2002 | Deweese et al. | |
| 2002/0133080 A1 | 9/2002 | Apruzzese et al. | |
| 2002/0137059 A1 | 9/2002 | Wu et al. | |
| 2003/0013941 A1 | 1/2003 | Cohn et al. | |
| 2003/0023187 A1 | 1/2003 | Tapper | |
| 2003/0040682 A1 | 2/2003 | Tapper | |
| 2003/0062262 A1 | 4/2003 | Mansouri et al. | |
| 2003/0098233 A1 | 5/2003 | Kermani et al. | |
| 2003/0109777 A1 | 6/2003 | Kloepfer et al. | |
| 2003/0157726 A1 | 8/2003 | Blum et al. | |
| 2003/0191415 A1 | 10/2003 | Moerman et al. | |
| 2003/0207441 A1 | 11/2003 | Eyster et al. | |
| 2003/0207454 A1 | 11/2003 | Eyster et al. | |
| 2004/0012676 A1 | 1/2004 | Weiner et al. | |
| 2004/0019653 A1 | 1/2004 | Debaty et al. | |
| 2004/0019686 A1 | 1/2004 | Toyoda et al. | |
| 2004/0047764 A1 | 3/2004 | Purcell | |
| 2004/0106858 A1 | 6/2004 | Say et al. | |
| 2004/0156832 A1 | 8/2004 | Jolly | |
| 2004/0171921 A1 | 9/2004 | Say et al. | |
| 2004/0200721 A1 | 10/2004 | Bhullar et al. | |
| 2004/0244151 A1 | 12/2004 | Sakata et al. | |
| 2004/0259180 A1 | 12/2004 | Burke et al. | |
| 2005/0016845 A1 | 1/2005 | Groll et al. | |
| 2005/0016846 A1 | 1/2005 | Groll et al. | |
| 2005/0019805 A1 | 1/2005 | Groll | |
| 2005/0019945 A1 | 1/2005 | Groll et al. | |
| 2005/0019953 A1 | 1/2005 | Groll et al. | |
| 2005/0023137 A1 | 2/2005 | Bhullar et al. | |
| 2005/0027181 A1 | 2/2005 | Goode, Jr. et al. | |
| 2005/0057676 A1 | 3/2005 | Weiner et al. | |
| 2005/0076845 A1 | 4/2005 | Langdale | |
| 2005/0079945 A1 | 4/2005 | Wittkopp | |
| 2005/0103624 A1 | 5/2005 | Bhullar et al. | |
| 2005/0121322 A1 | 6/2005 | Say et al. | |
| 2005/0137471 A1 | 6/2005 | Haar et al. | |
| 2005/0142033 A1 | 6/2005 | Glezer et al. | |
| 2005/0154271 A1 | 7/2005 | Rasdal et al. | |
| 2005/0161345 A1 | 7/2005 | Groll et al. | |
| 2005/0177072 A1 | 8/2005 | Kloepfer et al. | |
| 2005/0196747 A1 | 9/2005 | Stiene | |
| 2005/0199494 A1 | 9/2005 | Say et al. | |
| 2005/0226846 A1 | 10/2005 | Umlauf et al. | |
| 2005/0279647 A1 | 12/2005 | Beaty | |
| 2006/0042964 A1 | 3/2006 | Mansouri et al. | |
| 2006/0108218 A1 | 5/2006 | Gephart et al. | |
| 2006/0189895 A1 | 8/2006 | Neel et al. | |
| 2007/0110615 A1 | 5/2007 | Neel et al. | |
| 2007/0273904 A1 | 11/2007 | Robinson et al. | |
| 2008/0105024 A1 | 5/2008 | Creaven et al. | |
| 2009/0030617 A1 | 1/2009 | Schell et al. | |
| 2009/0125268 A1 | 5/2009 | Perry | |
| 2009/0205399 A1 | 8/2009 | Sun et al. | |

FOREIGN PATENT DOCUMENTS

| | | |
|---|---|---|
| EP | 1024358 | 8/2000 |
| EP | 1152239 | 11/2001 |
| EP | 1256798 | 11/2002 |
| EP | 1288653 | 3/2003 |
| EP | 1431758 | 6/2004 |
| EP | 1475630 | 11/2004 |
| EP | 1484603 | 12/2004 |
| EP | 1593961 | 11/2005 |
| EP | 1666605 | 6/2006 |
| JP | 2000 019147 | 1/2000 |
| JP | 2001-281197 | * 10/2001 |
| WO | WO 01/73420 | 10/2001 |
| WO | WO 03/019165 | 3/2003 |
| WO | WO 2004/113911 | 12/2004 |
| WO | WO 2004/113914 | 12/2004 |
| WO | WO 2004/113915 | 12/2004 |
| WO | WO 2005/001474 | 1/2005 |
| WO | WO 2006/035322 | 4/2006 |
| WO | WO 2006/113723 | 10/2006 |
| WO | WO 2006/113865 | 10/2006 |
| WO | WO 2007/078533 | 7/2007 |
| WO | WO 2007/100651 | 9/2007 |
| WO | WO 2008/057479 | 5/2008 |

OTHER PUBLICATIONS

International Search Report—PCT/US08/081572 dated Mar. 19, 2009 (5 pages).

Written Opinion—PCT/US08/081572 dated Mar. 19, 2009 (3 pages).

* cited by examiner

AUTO-CALIBRATING TEST SENSORS

This application claims the benefit of U.S. Provisional Application No. 61/002,052, filed Nov. 6, 2007, which is incorporated by reference in its entirety.

FIELD OF THE INVENTION

The present invention relates generally to test sensors that are adapted to determine an analyte concentration. More specifically, the present invention generally relates to auto-calibrating test sensors.

BACKGROUND OF THE INVENTION

The quantitative determination of analytes in body fluids is of great importance in the diagnoses and maintenance of certain physiological abnormalities. For example, lactate, cholesterol, and bilirubin should be monitored in certain individuals. In particular, it is important that diabetic individuals frequently check the glucose level in their body fluids to regulate the glucose intake in their diets. The results of such tests may be used to determine what, if any, insulin or other medication should be administered. In one type of blood-glucose testing system, test sensors are used to test a sample of blood.

A test sensor contains biosensing or reagent material that reacts with, for example, blood glucose. The testing end of the sensor is adapted to be placed into the fluid being tested (e.g., blood) that has accumulated on a person's finger after the finger has been pricked. The fluid may be drawn into a capillary channel that extends in the sensor from the testing end to the reagent material by capillary action so that a sufficient amount of fluid to be tested is drawn into the sensor. The tests are typically performed using optical or electrochemical testing methods.

Diagnostic systems, such as blood-glucose testing systems, typically calculate the actual glucose value based on a measured output and the known reactivity of the reagent-sensing element (e.g., test sensor) used to perform the test. The reactivity or lot-calibration information of the test sensor may be provided on a calibration circuit that is associated with the sensor package or the test sensor. This calibration circuit is typically physically inserted by the end user. In other cases, the calibration is automatically done using an auto-calibration circuit via a label on the sensor package or the test sensor. In this case, calibration is transparent to the end user and does not require that the end user insert a calibration circuit into the meter. Manufacturing millions of sensor packages, each having a calibration circuit or label to assist in calibrating the sensor package, can be expensive.

Therefore, it would be desirable to have a test sensor that provides calibration information thereon that may be manufactured in an efficient and/or cost-effective manner.

SUMMARY OF THE INVENTION

According to one aspect of the present invention, an electrochemical test sensor configured to determine an analyte concentration of a fluid sample is disclosed. The test sensor comprises a base including a first end and a second opposing end. The base further includes a first and second side bridging the first and second opposing end. The test sensor further comprises a plurality of electrodes formed on the base at or near the first end. The plurality of electrodes includes a working electrode and a counter electrode. The test sensor further comprises a first test-sensor contact formed on the base at or near the second opposing end. The first test-sensor contact is coupled to the working electrode by a first conductive lead. The test sensor further comprises a second test-sensor contact formed on the base at or near the second opposing end. The second test-sensor contact is coupled to the counter electrode by a second conductive lead. The positions of the first and second test-sensor contacts correspond with calibration information assigned to the test sensor.

According to one process, a method of making an electrochemical test sensor configured to assist in determining the concentration of an analyte in a fluid sample is disclosed. The method comprises the act of providing a base having a first end for receiving the fluid sample and a second opposing end for being placed in a meter. The base further includes a first and second side bridging the first end and the second opposing end. The method further includes the act of providing a plurality of electrodes formed on the base at or near a first end. The plurality of electrodes includes a working electrode and a counter electrode. The method further includes the act of assigning calibration information to the test sensor. The method further includes the act of providing a first test-sensor contact formed on the base at or near a second opposing end. The first test-sensor contact is coupled to the working electrode by a first conductive lead. The method further includes the act of providing a second test-sensor contact formed on the base at or near a second opposing end. The first test-sensor contact is coupled to the working electrode by a second conductive lead. The positions of the first and second test-sensor contacts on the base correspond to the calibration information.

According to another process, a method of using a test sensor and a meter, the test sensor and meter using calibration information in determining the concentration of an analyte in a fluid sample, is disclosed. The method comprises the act of providing a test sensor including a base. The base includes a first test-sensor contact positioned at or near a first end. The first test-sensor contact is coupled to a working electrode positioned at or near a second opposing end by a first conductive lead. The base further includes a second test-sensor contact positioned at or near the first end. The second test-sensor contact is coupled to a counter electrode positioned at or near the second opposing end by a second conductive lead. The test sensor has calibration information assigned thereto. The method further includes the act of providing a meter with a test-sensor opening. The meter includes an array of contact pins for contacting the first and second test-sensor contacts. The array of contact pins is positioned within test-sensor opening. The method further includes the act of placing the second opposing end of the test sensor into the test-sensor opening of the meter. The method further includes the act of contacting the test-sensor contacts with a first and second pin in the array of contact pins to detect the placement of the test-sensor contacts. The method further includes the act of determining the calibration information associated with the test sensor by which first and second pins contact the first and second meter contacts.

Figure 1A:
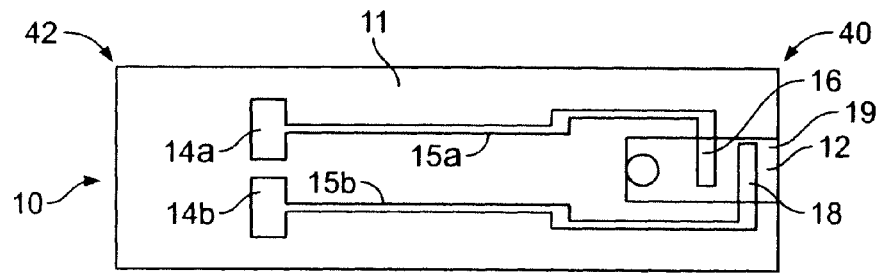
FIG. 1*a* is a test sensor according to one embodiment.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION OF ILLUSTRATED EMBODIMENTS

Generally, an instrument or meter uses a test sensor adapted to receive a fluid sample to be analyzed and a processor adapted to perform a predefined test sequence for measuring a predefined parameter value. A memory is coupled to the processor for storing predefined parameter data values. Calibration information associated with the test sensor may be read by the processor before or after the fluid sample to be measured is received, but not after the analyte concentration has been determined. Calibration information is generally used to compensate for different characteristics of test sensors, which will vary on a batch-to-batch basis. In some systems, the calibration information is provided on an auto-calibration circuit or label that is associated with each test sensor batch.

The calibration information may be, for example, the lot specific reagent calibration information for the test sensor. The calibration information may be in the form of a calibration code. Selected information associated with the test sensor (which may vary on a batch-to-batch basis) is tested to determine the calibration information to be used in association with the meter.

The present invention is directed to an improved method of making a test sensor that is adapted to assist in determining an analyte concentration. In one embodiment, a test sensor is adapted to receive a fluid sample and is analyzed using an instrument or meter. Analytes that may be measured include glucose, lipid profiles (e.g., cholesterol, triglycerides, LDL, and HDL), microalbumin, hemoglobin $A_{1C}$, fructose, lactate, or bilirubin. It is contemplated that other analyte concentrations may be determined. The analytes may be in, for example, a whole blood sample, a blood serum sample, a blood plasma sample, other body fluids like ISF (interstitial fluid), creatinine, urea, urine, and non-body fluids. As used within this application, the term "concentration" refers to an analyte concentration, activity (e.g., enzymes and electrolytes), titers (e.g., antibodies), or any other means used to measure the desired analyte.

The test sensors described herein may be electrochemical test sensors. In such embodiments, the meter may have optical aspects so as to detect the calibration information and electrochemical aspects to determine the analyte concentration of the fluid sample. One non-limiting example of an electrochemical test sensor is shown in FIG. 1a. FIG. 1a depicts a test sensor 10 including a base 11, a capillary channel, and a plurality of electrodes 16 and 18. A region 12 shows an area that defines the capillary channel (e.g., after a lid is placed over the base 11). The plurality of electrodes includes a counter electrode 16 and a working (measuring) electrode 18. The electrochemical test sensor may also contain at least three electrodes, such as a working electrode, an auxiliary or "counter" electrode, a trigger electrode, or a hematocrit electrode. The electrodes 16, 18 are coupled to a plurality of conductive leads 15a,b, which, in the illustrated embodiment, terminate with a larger area designated as a test-sensor contact 14a,b. The capillary channel is generally located in a fluid-receiving area 19. Examples of electrochemical test sensors, including their operation, may be found in, for example, U.S. Pat. No. 6,531,040 assigned to Bayer Corporation. It is contemplated that other electrochemical test sensors may be employed.

The fluid-receiving area 19 includes at least one reagent for converting the analyte of interest (e.g., glucose) in the fluid sample (e.g., blood) into a chemical species that is electrochemically measurable, in terms of the electrical current it produces, by the components of the electrode pattern. The reagent typically contains an enzyme such as, for example, glucose oxidase, which reacts with the analyte and with an electron acceptor such as a ferricyanide salt to produce an electrochemically measurable species that can be detected by the electrodes. It is contemplated that other enzymes may be used to react with glucose such as glucose dehydrogenase. If the concentration of another analyte is to be determined, an appropriate enzyme is selected to react with the analyte.

A fluid sample (e.g., blood) may be applied to the fluid-receiving area 19. The fluid sample reacts with the at least one reagent. After reacting with the reagent and in conjunction with the plurality of electrodes, the fluid sample produces electrical signals that assist in determining the analyte concentration. The conductive leads 15a,b carry the electrical signal back toward a second opposing end 42 of the test sensor 10 where test-sensor contacts 14a,b transfer the electrical signals into the meter.

Figure 1B:
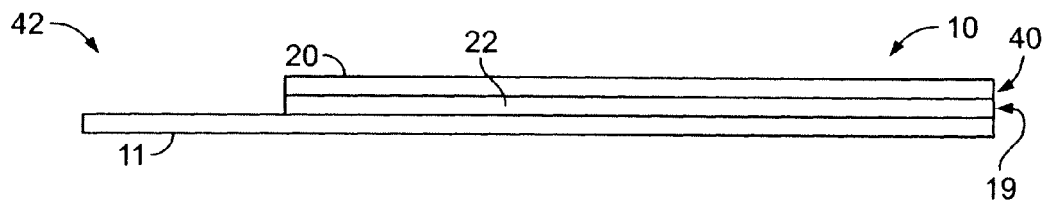
FIG. 1*b* is a side view of the test sensor of FIG. 1*a*.

Referring to FIG. 1b, a side view of the test sensor 10 of FIG. 1a is shown. As shown in FIG. 1b, the test sensor 10 of FIG. 1b further includes a lid 20 and a spacer 22. The base 11, the lid 20, and the spacer 22 may be made from a variety of materials such as polymeric materials. Non-limiting examples of polymeric materials that may be used to form the base 11, the lid 20, and the spacer 22 include polycarbonate, polyethylene terephthalate (PET), polyethylene naphthalate (PEN), polyimide, and combinations thereof. It is contemplated that other materials may be used in forming the base 11, lid 20, and/or spacer 22.

To form the test sensor 10 of FIGS. 1a, 1b, the base 11, the spacer 22, and the lid 20 are attached by, for example, an adhesive or heat sealing. When the base 11, the lid 20, and the spacer 22 are attached, a fluid-receiving area 19 is formed. The fluid-receiving area 19 provides a flow path for introducing the fluid sample into the test sensor 10. The fluid-receiving area 19 is formed at a first end or testing end 40 of the test sensor 10.

Figure 2:
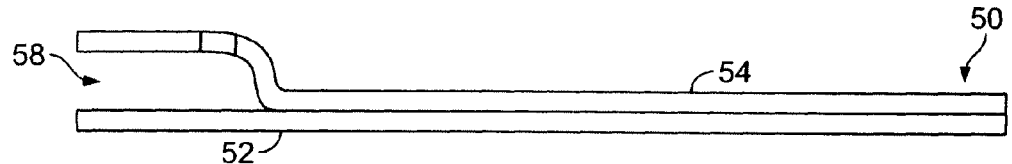
FIG. 2 is a cross-sectional view of a test sensor according to another embodiment.

It is contemplated that the test sensors of the embodiments of the present invention may be formed with a base and a lid in the absence of a spacer. In one such embodiment, a lid may be formed with a convex opening that is adapted to receive a fluid. A non-limiting example of such a test sensor is shown in FIG. 2. Specifically, in FIG. 2, a test sensor 50 includes a base 52 and a lid 54. When the lid 54 is attached to the base 52, a fluid-receiving area 58 is formed that is adapted to receive fluid for testing.

The test sensors of the embodiments described herein may be optical test sensors. Optical test sensor systems may use techniques such as, for example, transmission spectroscopy, diffuse reflectance, or fluorescence spectroscopy for measuring the analyte concentration. An indicator reagent system and an analyte in a sample of body fluid are reacted to produce a chromatic reaction, as the reaction between the reagent and analyte causes the sample to change color. The degree of color change is indicative of the analyte concentration in the body fluid. The color change of the sample is evaluated to measure the absorbance level of the transmitted light. Transmission spectroscopy is described in, for example, U.S. Pat. No. 5,866,349. Diffuse reflectance and fluorescence spectroscopy are described in, for example, U.S. Pat. No. 5,518,689 (titled "Diffuse Light Reflectance Read Head"), U.S. Pat. No. 5,611, 999 (titled "Diffuse Light Reflectance Read Head"), and U.S. Pat. No. 5,194,393 (titled "Optical Biosensor and Method of Use").

Figure 3:
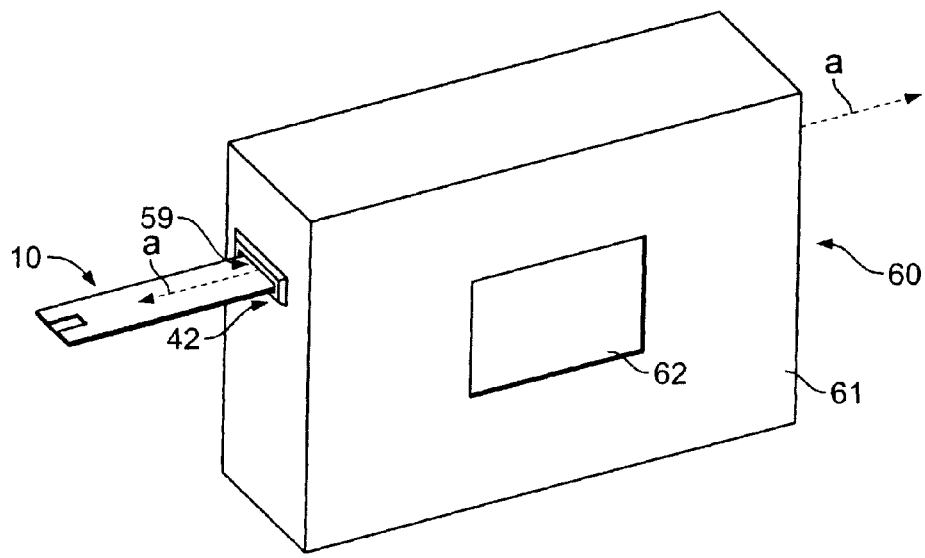
FIG. 3 is an isometric view of an instrument or meter for receiving the test sensors of the embodiments of the present invention.
Figure 4A:
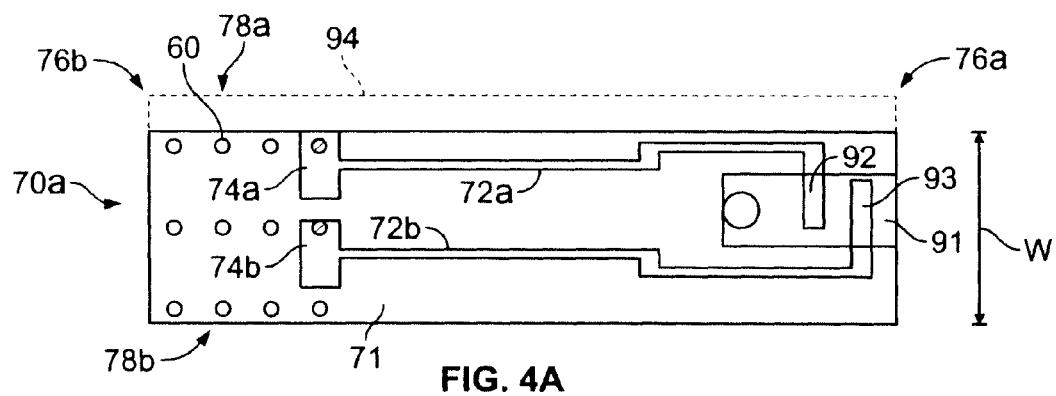
FIGS. 4a, 4b, 4c, 4d, 4e, 4f, 4g, and 4h are top views of test sensors according to embodiments of the present invention.
Figure 4B:
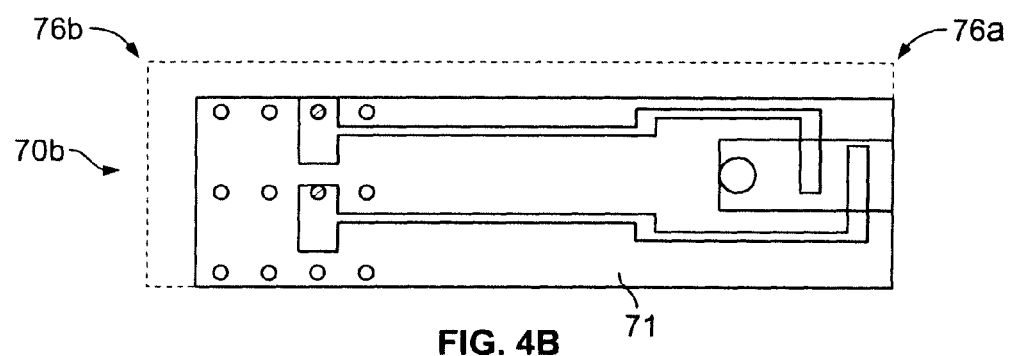
Figure 4C:
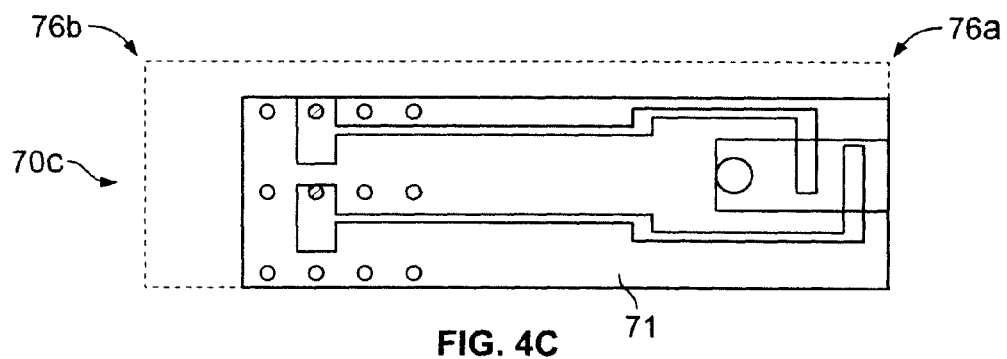
Figure 4D:
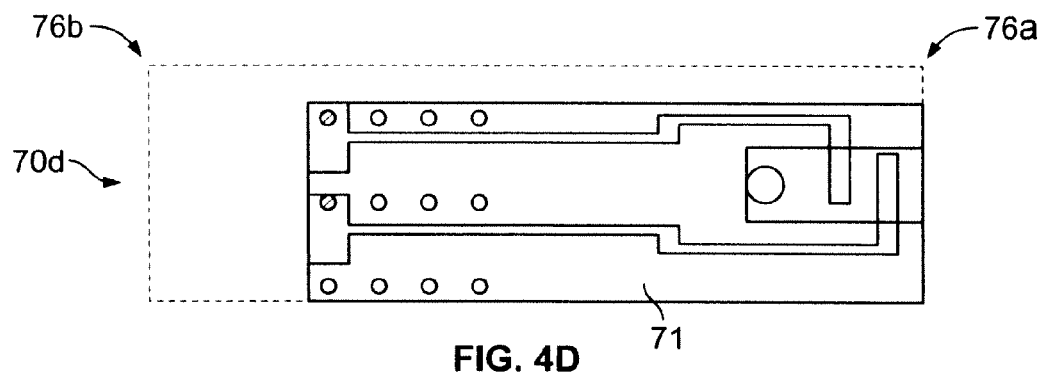
Figure 4E:
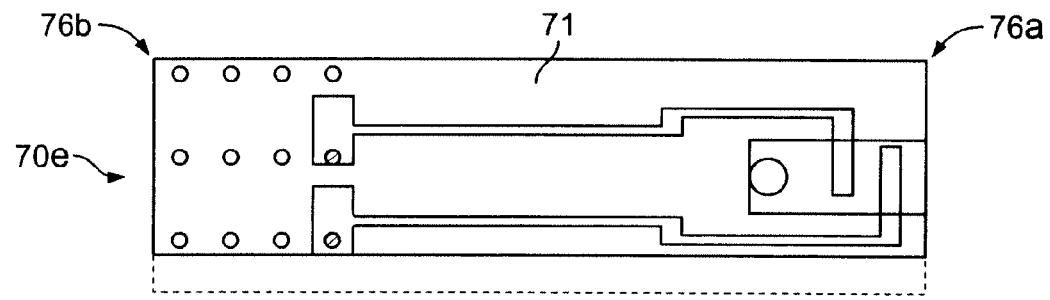
Figure 4F:
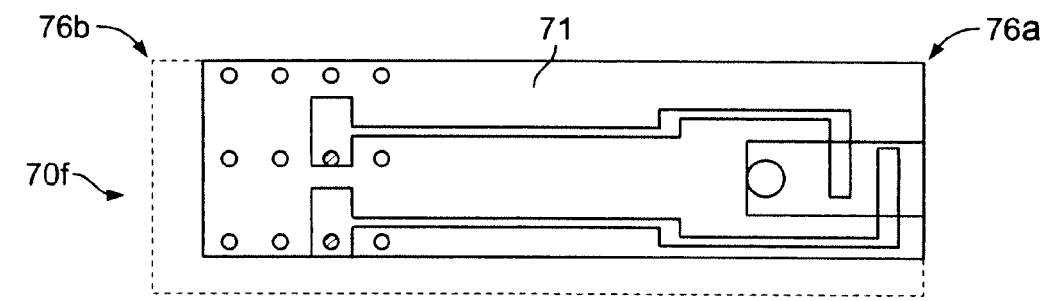
Figure 4G:
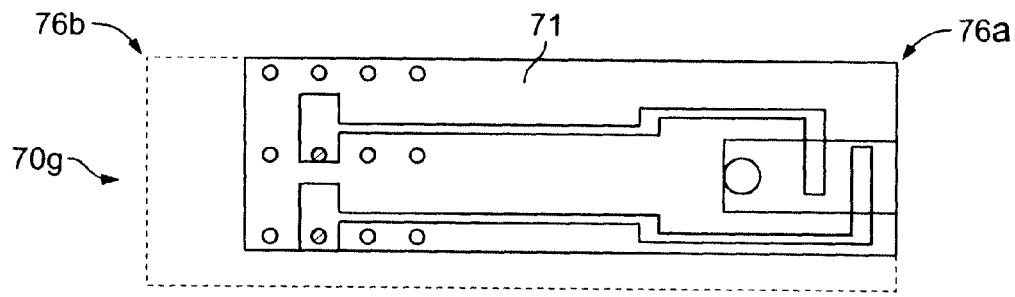
Figure 4H:
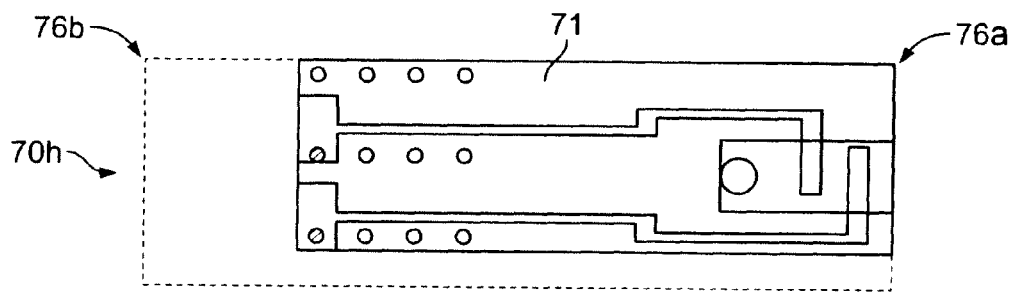

Referring back to FIGS. 1a,b, the second opposing end 42 of the test sensor 10 is adapted to be placed into a test-sensor opening 59 in an instrument or meter 60, as shown, for example, in FIG. 3. FIG. 3 depicts a single-sensor instrument or meter 60. The meter 60 comprises a housing 61 that forms the test-sensor opening 59, which is of sufficient size to receive the second opposing end 42 of the test sensor 10. After the calibration information of the test sensor 10 has been determined, the meter 60 uses, for example, the appropriate program number during calculation of the analyte concentration by the meter software. The meter housing 61 may comprise a display 62 (e.g., an LCD screen) that displays, for example, analyte concentrations.

According to one embodiment of the present invention, calibration information of test sensors is determined by the position of the test-sensor contacts on the test sensors. Referring to FIGS. 4a-h, for example, test sensors 70a-h are illustrated according to one embodiment of the present invention. The test sensors 70a-h are generally similar to the test sensor 10 of FIGS. 1a,b. For example, the test sensors 70a-h include a testing end 76a and a second opposing end 76b. The test sensors 70a-h further include a base 71, a capillary channel 91, and a plurality of electrodes 92, 93 coupled to respective conductive leads 72a,b, which terminate with test-sensor contacts 74a,b.

Figure 5:
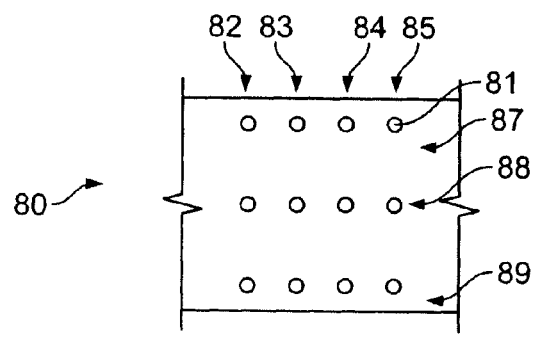
FIG. 5 is a top view of an array of pins adapted to be used with the meter of FIG. 3 and the test sensors of FIGS. 4a-h.

The test sensors 70a-h of FIGS. 4a-h are adapted to be used with a meter having an array of contact pins housed within the meter. FIG. 5 illustrates a top view of one non-limiting example of an array of pins 80 that may be used in a meter adapted to be used with the test sensors 70a-h. Although the array of pins 80 includes twelve pins 81 positioned in four columns 82-85 and three rows 87-89, the array 80 may include any number of pins, rows, and/or columns. The array of pins 80 generally extends from a top or bottom interior surface of the meter within and near the back or inner portion of the test-sensor opening (e.g., opening 59 of FIG. 3) such that the array of pins 80 may contact the test sensor 70a-h when the test sensor 70a-h is placed within the opening 59. Contact points 60 are shown on each of the test sensors 70a-h to demonstrate where the array of pins 80 would contact the test sensors 70a-h when in use. These contact points 60 may or may not be visible on the actual test sensors 70a-h.

According to one embodiment of the present invention, the positions of the test-sensor contacts of the test sensors are varied during production to correspond with calibration information associated with the test sensors. Specifically, the test-sensor contacts are positioned to contact a specific one or more pins in the array of pins housed within a meter. Each of the pins and/or certain combinations of pins in the array correspond with different calibration information. The meter may detect which pins contact the test-sensor contacts and, thus, apply the corresponding calibration information (e.g., a certain program number or code).

Referring back to FIGS. 4a-h, the calibration information for the test sensors 70a-h was determined to be different, and, thus, the placement of the test-sensor contacts 74a,b on the test sensors 70a-h vary accordingly. In the embodiments of FIGS. 4a-h, the positions of the test-sensor contacts 74a,b vary by (a) the length of the test sensors 70a-h, and (b) the position of the test-sensor contacts 74a,b relative to the first and second sides 78a,b of the test sensors 70a-h.

Because the testing components (e.g., capillary channel 91, electrodes 92, 93, conductive leads 72a,b, test-sensor contacts 74a,b) of the test sensors 70a-h are generally the same and have the same dimensions, the test sensors 70a-h may be formed from a continuous web of material. Furthermore, the testing components may be uniformly printed on all of the test sensors 70a-h during a single manufacturing process. This may be desirable for minimizing manufacturing costs.

The test sensors 70a-h may then be cut from the continuous web of material. The test sensors 70a-h of FIGS. 4a-h are cut such that the testing components of all of the test sensors 70a-h are positioned a generally equal distance from the testing end 76a of the test sensors 70a-h. The second opposing ends 76b of the test sensors 70a-h have been cut such that the length of the test sensors 70a-h and the distance between the test-sensor contacts 74a,b and the second opposing end 76b is varied. Thus, the test-sensor contacts 74a,b of the test sensors 70a-h may contact different columns 82-85 of pins 81 corresponding with calibration information associated with each test sensor 70a-h. For example, the test sensors 70d,h of FIGS. 4d,h are cut such that the test-sensor contacts 74a,b are positioned adjacent to or nearly adjacent to the second opposing end 76b. Thus, when the second opposing end 76b of the test sensors 70d,h are placed within an opening of a meter (see FIG. 3), the test-sensor contacts 74a,b will contact the pins 81 positioned in the first column 82 of the array of pins 80. The length of the shortest test sensors 70d,h should be at least as long as the test-sensor opening (e.g., opening 59) of the meter with which they are to be used so that the test sensors 70d,h may be fully inserted and removed from the opening. The test-sensor contacts 74a,b of the test sensors 70c,g of FIGS. 4c,g are positioned a greater distance from the second opposing ends 76b and, thus, will contact pins 81 in the second column 83 of the array of pins 80. The test sensors 70b,f of FIGS. 4b,f will contact pins 81 in the third column 84 of the array of pins 80. Finally, the test sensors 70a,e of FIGS. 4a,e, which have not been reduced in length, will contact pins 81 in the fourth column 85 of the array of pins 80.

Moreover, although the width W of the test sensors 70a-h is generally the same, the test sensors 70a-h may also be cut such that the position of the testing components (e.g., the test-sensor contacts 74a,b) relative to the first and second sides 78a,b of each test sensor 70a-h is varied. This may be done by cutting off a portion of the base 71 along the first or second side 78a,b of the test sensor 70a-h such that the test-sensor contacts 74a,b of the test sensors 70a-h may contact different rows 87-89 of pins 81. Thus, the test sensors 70a-h may contact different rows 87-89 of pins 81 corresponding with calibration information associated with each test sensor 70a-h. For example, a portion of the base 71 adjacent to the first side 78a of the test sensors 70a-d of FIGS. 4a-d is cut such that when the test sensors 70a-d are placed within an opening of a meter (see FIG. 3), the test-sensor contacts 74a,b will contact the pins 81 positioned in the first and second rows 87, 88 of the array of pins 80. A portion of the base 71 adjacent to the second side 78b of the test sensors 70e-h of FIGS. 4e-h are cut such that when the test sensors 70e-h are placed within an opening of a meter (see FIG. 3), the test-sensor contacts 74a,b will contact the pins 81 positioned in the second and third rows 88, 89 of the array of pins 80.

By varying the length of the test sensors 70a-h and the positions of the test-sensor contacts 74a,b on the test sensors 70a-h, all of the test sensors 70a-h, which have been determined to have different calibration information associated therewith, may contact different combination of pins 81 when inserted into a meter opening. Thus, the appropriate calibration information may be determined and applied. The dashed lines 94 of FIGS. 4*a-h* indicate the portions of the test sensors 70*a-h* that have been cut to vary the length and the position of the test-sensor contacts 74*a,b*.

Aspects of the test sensors other than or including the length of the embodiments of the present invention may also be varied to ensure that the test-sensor contacts of test sensors having different calibration information contact different pins or combinations of pins in a meter. The test-sensor contacts of the test sensors illustrated and described above with respect to FIGS. 4*a-h* may contact adjacent pins (see FIGS. 4*a-h*), non-adjacent pins, pins in different columns and/or rows, or combinations thereof. It is also contemplated that the calibration information associated with a test sensor may be determined by the position of a single test-sensor contact and/or a single pin contacted by the test-sensor contact. For example, the position of a test-sensor contact coupled to a working electrode and/or a pin contacted by the test-sensor contact coupled to the working electrode may not effect the determination of which calibration information to apply. Furthermore, it is contemplated that the test-sensor contacts may have positions other than those shown in FIGS. 4*a-h*. It is also contemplated that the testing components may be different (e.g., have different dimensions) that those of FIGS. 4*a-h*.

According to one embodiment, a meter (e.g., meter 60 of FIG. 3) to be used with the test sensors described above with respect to FIGS. 4*a-h* includes a mechanism for raising and lowering the array of pins (e.g., array 80 of FIG. 5) within the meter. The raised position may be a default position for the array of pins 80 so that the second opposing end of a test sensor may be readily received by the meter via the test-sensor opening (e.g., opening 59 of FIG. 3). Once the second opposing end of the test sensor is positioned within the test-sensor opening, the array of pins may be lowered to contact the test sensor and the test-sensor contacts positioned thereon. Any suitable mechanism may be used to raise and/or lower the array of pins within the meter including, for example, mechanical switches and electronics.

All of the sensors and assemblies described herein may be desirable because they may support many different types of calibration information. The test sensors may be used as single stand-alone test sensors. The test sensors may also be stored in a cartridge.

In the embodiments described herein, it is important that the test sensors are fully inserted into the test-sensor opening for the calibration information to be correctly ascertained. Thus, the meters used with the test sensors may include a mechanism for determining whether the test sensors are fully inserted. The mechanism may be positioned, for example, in or adjacent to the test-sensor opening. The meter may further be adapted to report an error to a user if it detects that the test sensor is not fully inserted.

The calibration information referred to herein may be any information that may be used by a meter or instrument. For example, the calibration information may be a program auto-calibration number that relates to a slope and intercept of calibration lines for the test sensor lot or batch. In addition to calibration information, other information may be contained such an analyte type or manufacturing date.

According to alternative embodiment A, an electrochemical test sensor configured to determine an analyte concentration of a fluid sample, the electrochemical test sensor comprises a base including a first end and a second opposing end, the base further including a first and second side bridging the first and second opposing end, a plurality of electrodes formed on the base at or near the first end, the plurality of electrodes including a working electrode and a counter electrode, a first test-sensor contact formed on the base at or near the second opposing end, the first test-sensor contact being coupled to the working electrode by a first conductive lead, and a second test-sensor contact formed on the base at or near the second opposing end, the second test-sensor contact being coupled to the counter electrode by a second conductive lead, wherein the positions of the first and second test-sensor contacts correspond with calibration information assigned to the test sensor.

According to alternative embodiment B, the test sensor of alternative embodiment A, wherein the position of the test-sensor contacts relative to the second opposing end corresponds to the calibration information.

According to alternative embodiment C, the test sensor of alternative embodiment B, wherein the position of the test-sensor contacts relative to the first and second sides further corresponds to the calibration information.

According to alternative embodiment D, the test sensor of alternative embodiment A, wherein the length of the base corresponds with the calibration information, the length being the distance from the first end and the second opposing end.

According to alternative process E, a method of making an electrochemical test sensor configured to assist in determining the concentration of an analyte in a fluid sample, the method comprises the acts of providing a base having a first end for receiving the fluid sample and a second opposing end for being placed in a meter, the base further including a first and second side bridging the first end and the second opposing end, providing a plurality of electrodes formed on the base at or near a first end, the plurality of electrodes including a working electrode and a counter electrode, assigning calibration information to the test sensor, providing a first test-sensor contact formed on the base at or near a second opposing end, the first test-sensor contact being coupled to the working electrode by a first conductive lead, and providing a second test-sensor contact formed on the base at or near a second opposing end, the first test-sensor contact being coupled to the working electrode by a second conductive lead, wherein the positions of the first and second test-sensor contacts on the base correspond to the calibration information.

According to alternative process F, the method of alternative process E, wherein the act of providing a base includes providing a plurality of bases formed on a continuous web.

According to alternative process G, the method of alternative process F further including separating each of the plurality of bases from the continuous web.

According to alternative process H, the method of alternative process G, wherein the act of separating includes varying the length of the plurality of bases, the length being the distance from the first end and the second opposing end, the length corresponding to the calibration information.

According to alternative process I, the method of alternative process E, wherein the position of the test-sensor contacts relative to the second opposing end corresponds to the calibration information.

According to alternative process J, the method of alternative process I, wherein the position of the test-sensor contacts relative to the first and second sides further corresponds to the calibration information.

According to alternative process K, a method of using a test sensor and a meter, the test sensor and meter using calibration information in determining the concentration of an analyte in a fluid sample, the method comprises the acts of providing a test sensor including a base, the base including a first test-sensor contact positioned at or near a first end, the first test-sensor contact being coupled to a working electrode positioned at or near a second opposing end by a first conductive lead, the base further including a second test-sensor contact positioned at or near the first end, the second test-sensor contact being coupled to a counter electrode positioned at or near the second opposing end by a second conductive lead, the test sensor having calibration information assigned thereto, providing a meter with a test-sensor opening, the meter including an array of contact pins for contacting the first and second test-sensor contacts, the array of contact pins being positioned within test-sensor opening, placing the second opposing end of the test sensor into the test-sensor opening of the meter, contacting the test-sensor contacts with a first and second pin in the array of contact pins to detect the placement of the test-sensor contacts, and determining the calibration information associated with the test sensor by which first and second pins contact the first and second meter contacts.

According to alternative process L, the method of alternative process K, wherein the act of providing a test sensor including a base includes providing a plurality of bases formed on a continuous web.

According to alternative process M, the method of alternative process L further including separating each of the plurality of bases from the continuous web.

According to alternative process N, the method of alternative process M, wherein the act of separating includes varying the length of the plurality of bases, the length being the distance from the first end and the second opposing end, the length corresponding to the calibration information.

According to alternative process O, the method of alternative process K, wherein the position of the test-sensor contacts relative to the second opposing end corresponds to the calibration information.

According to alternative process P, the method of alternative process O, wherein the position of the test-sensor contacts relative to the first and second sides further corresponds to the calibration information.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents, and alternatives falling within the spirit and scope of the invention.

What is claimed is:

1. A method of making an electrochemical test sensor configured to assist in determining the concentration of an analyte in a fluid sample, the method comprising the acts of:
    forming a plurality of electrodes on a test-sensor base, the plurality of electrodes including a working electrode and a counter electrode;
    forming a first test-sensor contact on the test-sensor base, the first test-sensor contact being coupled to the working electrode by a first conductive lead; and
    forming a second test-sensor contact on the test-sensor base, the second test-sensor contact being coupled to the counter electrode by a second conductive lead;
    after forming the first and second test-sensor contacts, determining calibration information to be used with the electrochemical test sensor; and
    after determining the calibration information, cutting at least one side or end of the test-sensor base based on the calibration information such that the positions of the first and second test-sensor contacts on of the test-sensor base correspond to the calibration information associated with the electrochemical test sensor.

2. The method of claim 1, wherein the acts of forming a plurality of electrodes and forming the first and second test-sensor contacts are performed on a continuous web of material.

3. The method of claim 2, wherein the act of cutting at least one side or end of the test-sensor base includes separating the test-sensor base from the continuous web.

4. The method of claim 2, wherein the continuous web of material includes a plurality of test-sensor bases, the first and second test-sensor contacts being uniform among the plurality of test-sensor bases, wherein the act of cutting includes separating each of the plurality of test-sensor bases from one another such that at least two different types of electrochemical test sensors are formed, each of the different types of test sensors having different calibration information associated therewith.

5. The method of claim 1, wherein the act of cutting at least one side or end of the test-sensor base includes adjusting the length of the test-sensor base, the length being the distance from a testing end and a second opposing end of the test-sensor base.

6. The method of claim 5, wherein the position of the test-sensor contacts relative to the second opposing end corresponds to the calibration information.

7. The method of claim 1, wherein the test-sensor base includes a first and second side bridging a testing end and a second opposing end, the position of the test-sensor contacts relative to the first and second sides corresponding to the calibration information.

8. A method of associating calibration information with a test sensor configured to determine the concentration of an analyte in a fluid sample, the method comprising the acts of:
    forming at least one test-sensor base having a first test-sensor contact and a second test-sensor contact, the first test-sensor contact being coupled to a working electrode by a first conductive lead, the second test-sensor contact coupled to a counter electrode by a second conductive lead;
    after forming the first and second test-sensor contacts, determining calibration information to be used with the test sensor;
    after determining the calibration information, forming at least one test sensor by cutting at least one of a testing end, a second opposing end, and a first and second side bridging the testing and second end of the test-sensor base based on the calibration information such that the positions of the first and second test-sensor contacts on the test sensor correspond to the calibration information associated with the test sensor, the working and counter electrodes being positioned at or near the testing end and the first and second test-sensor contacts being positioned at or near the second end;
    providing a meter with a test-sensor opening, the meter including an array of contact pins for contacting the first and second test-sensor contacts, the array of contact pins being positioned within test-sensor opening;
    placing the second end of the test sensor into the test-sensor opening of the meter;
    contacting the test-sensor contacts with a first and second pin in the array of contact pins to detect the placement of the test-sensor contacts; and
    determining the calibration information associated with the test sensor by which first and second pins contact the first and second test-sensor contacts.

9. The method of claim 8, wherein the act of forming the test sensor includes cutting the length of the test-sensor base, the length being the distance from the testing end and the second opposing end, the length corresponding to the calibration information.

10. The method of claim 8, wherein the position of the test-sensor contacts relative to the second opposing end corresponds to the calibration information.

11. The method of claim 8, wherein the position of the test-sensor contacts relative to the first and second sides corresponds to the calibration information.

12. The method of claim 8, wherein the act of forming the at least one test-sensor base includes forming a plurality of test-sensor bases, the first and second test-sensor contacts being uniform among the plurality of test-sensor bases.

13. The method of claim 12, wherein the plurality of test sensors are formed on a continuous web of material.

14. The method of claim 13, wherein the act of cutting forms at least two different types of test sensors having different calibration information associated therewith.

* * * * *

UNITED STATES PATENT AND TRADEMARK OFFICE
CERTIFICATE OF CORRECTION

| | | |
|---|---|---|
| PATENT NO. | : 8,241,488 B2 | Page 1 of 1 |
| APPLICATION NO. | : 12/249283 | |
| DATED | : August 14, 2012 | |
| INVENTOR(S) | : Greg P. Beer | |

It is certified that error appears in the above-identified patent and that said Letters Patent is hereby corrected as shown below:

In column 10, line 1 (claim 1, line 19), please delete the word "of".

Signed and Sealed this
Fifth Day of February, 2013

Teresa Stanek Rea
*Acting Director of the United States Patent and Trademark Office*